(12) United States Patent
Tung et al.

(10) Patent No.: US 12,171,471 B2
(45) Date of Patent: Dec. 24, 2024

(54) BONE SCREW KIT

(71) Applicant: Socko Medical Co., Ltd., New Taipei (TW)

(72) Inventors: Jung-Tsou Tung, New Taipei (TW); Hao-Yun Tung, New Taipei (TW); Chang-Yi Kuo, New Taipei (TW); Wei-Han Ceng, New Taipei (TW); Chi-Yen Yang, New Taipei (TW)

(73) Assignee: Socko Medical Co., Ltd., New Taipei (TW)

( * ) Notice: Subject to any disclaimer, the term of this patent is extended or adjusted under 35 U.S.C. 154(b) by 310 days.

(21) Appl. No.: 17/940,098

(22) Filed: Sep. 8, 2022

(65) Prior Publication Data

US 2023/0389969 A1 Dec. 7, 2023

(30) Foreign Application Priority Data

Jun. 1, 2022 (CN) .......................... 202210620844.0

(51) Int. Cl.
*A61B 17/70* (2006.01)
*A61B 17/88* (2006.01)
*A61B 90/00* (2016.01)

(52) U.S. Cl.
CPC ...... *A61B 17/7091* (2013.01); *A61B 17/7005* (2013.01); *A61B 17/7032* (2013.01); *A61B 17/7076* (2013.01); *A61B 17/7082* (2013.01); *A61B 17/7085* (2013.01); *A61B 17/8875* (2013.01); *A61B 2090/037* (2016.02)

(58) Field of Classification Search
CPC ............ A61B 17/7091; A61B 17/7076; A61B 17/7082; A61B 17/7085
See application file for complete search history.

(56) References Cited

U.S. PATENT DOCUMENTS

| 6,743,231 B1* | 6/2004 | Gray | A61B 17/7091 606/279 |
|---|---|---|---|
| 8,439,922 B1* | 5/2013 | Arnold | A61B 17/708 606/279 |
| 2004/0158247 A1* | 8/2004 | Sitiso | A61B 17/7091 606/907 |
| 2004/0254576 A1* | 12/2004 | Dunbar, Jr. | A61F 2/4611 606/279 |
| 2005/0149053 A1* | 7/2005 | Varieur | A61B 17/7091 606/104 |

(Continued)

*Primary Examiner* — David W Bates
(74) *Attorney, Agent, or Firm* — Locke Lord LLP; Tim Tingkang Xia, Esq.

(57) ABSTRACT

A bone screw kit includes a support member, a screw, an extension sleeve, a connecting rod, a locking screw, a screw driver and an extension sleeve remover. The support member has two wings. An external wall of one axial end of the screw driver has ribs and one first snap. The first snap has oppositely a first outer diameter and a second outer diameter less than the first outer diameter. A through hole having a second snap is disposed on the locking screw furnished thereinside with grooves. The second snap has a first inner diameter less than the first outer diameter but larger than the second outer diameter. The locking screw and the screw driver are disposed in the support member and the extension sleeve. The extension sleeve having two extension wings sleeves the support member. Engagement structures are provide to engage the wing and the inner extension wing.

10 Claims, 17 Drawing Sheets

(56) References Cited

U.S. PATENT DOCUMENTS

| | | | | |
|---|---|---|---|---|
| 2006/0069391 | A1* | 3/2006 | Jackson | A61B 17/7001 606/62 |
| 2008/0051794 | A1* | 2/2008 | Dec | A61B 17/7032 606/105 |
| 2011/0166606 | A1* | 7/2011 | Stihl | A61B 17/7086 606/279 |
| 2014/0277137 | A1* | 9/2014 | Stad | A61B 17/708 606/86 A |
| 2014/0277206 | A1* | 9/2014 | Reitblat | A61B 17/708 606/86 A |
| 2015/0066089 | A1* | 3/2015 | Nelson | A61B 17/7002 606/86 A |
| 2016/0287293 | A1* | 10/2016 | Karas | B65D 51/28 |
| 2016/0331420 | A1* | 11/2016 | Dandanopoulos | A61B 17/708 |
| 2018/0271566 | A1* | 9/2018 | Fischer | A61B 17/7079 |
| 2019/0117270 | A1* | 4/2019 | Biedermann | A61B 17/7032 |
| 2019/0209214 | A1* | 7/2019 | Biedermann | A61B 17/708 |
| 2019/0307493 | A1* | 10/2019 | Jackson | A61B 17/7091 |
| 2020/0121397 | A1* | 4/2020 | Elliott | A61B 17/7074 |
| 2021/0186575 | A1* | 6/2021 | Biedermann | A61B 17/7032 |
| 2022/0133360 | A1* | 5/2022 | Papenfuss | A61B 17/7076 606/279 |

* cited by examiner

BONE SCREW KIT

CROSS REFERENCE TO RELATED APPLICATION

This application claims the benefits of Chinese application Serial No. 202210620844.0, filed on Jun. 1, 2022, the disclosures of which are incorporated by references herein in its entirety.

TECHNICAL FIELD

The present disclosure relates in general to a medical technology, and more particularly to a bone screw kit for locking a spinal connecting rod.

BACKGROUND

For patients with spinal disorders, it is easy to cause problems such as displacement, lesions, and atrophy of the intervertebral disc, from which possible shrinkage of the spinal process space may lead to depress the spinal nerve and cause the patient to have paralysis or pain in the back.

To solve the aforesaid problems, a current common treatment method is to carry out a minimally invasive surgery in which a rod for supporting the relative distance and position between the vertebral bodies would be implanted into the spine by using a number of bone screws.

According to the length, the bone screws can be divided into "short-winged screws" and "long-winged screws". The long-winged screws are further divided into two types: an open type and a closed type. In a typical minimally invasive surgery, since the opening at the patient is small but deep, thus, if a short-winged screw is used, an additional expander must be applied to expand the opening for facilitating the operation. Therefore, in terms of practicality and convenience, the open-type long-winged screw that can simplify the operation is much more popular than the short-winged screw in the art.

In particular, in a conventional open-type long-winged screw or bone screw, a positioning sleeve (or socket) and a screw are included. The positioning sleeve includes a fixing seat and a calibration sleeve integrated as a unique piece. The screw provided to the fixing seat by engaging an internal thread thereof is protruded over the fixing seat. The calibration sleeve is used for calibration during surgery. In the surgery, the screw as well as the positioning sleeve are screwed to the spine. After a spinal connecting rod engages the calibration sleeve, a locking screw is applied to the fixed seat so as to tighten the spinal connecting rod. Then, the calibration sleeve can be broken off and thus removed away.

However, many deficiencies in the above-mentioned conventional open-ended long-winged bone screws are found at least as follows.

(1) To implant the screw, install the spinal connecting rod, fasten the locking screw, break and then remove the calibration sleeve, different tools must be applied, and thus the entire surgical procedure would be pretty complicated.

(2) Since the connecting structure to be broken off between the calibration sleeve and the fixed seat is too thin to avoid accidental hits or bents by external forces such as hand tools during the operation, so accuracy of implanting the spinal connecting rod would be affected.

(3) Since fastening of the locking screw by the screw driver can only be "detected" by operator's experience and feeling, thus two situations are usually met. One is that the spinal connecting rod isn't enough tightened due to insufficient tightness at the locking screw, and another is that the locking screw or fixing seat must be replaced due to excessive tightening or screw slips at the locking screw.

In addition, another socket type of long-winged bone screw is introduced to have mainly a screw head, a screw and a long cylindrical expander to be sleeved on the screw head. The screw, screwed to protrude over the screw head, has a shape similar to a short-winged screw. Both the screw head and the expander for calibration during surgery have individual internal threads. While in a surgery, the screw as well as the positioning sleeve are screwed to the spine, the spinal connecting rod is then positioned, and a rod-shaped tool with external thread and the locking screw are then screwed to the expander. After the locking screw is tightened against the spinal connecting rod, then the expander can be removed.

Though the above-mentioned conventional socket-type long-winged bone screws can avoid some of the defects of the conventional open-type long-winged bone screws, yet many defects as follows are still there to be overcome.

(1) When the rod-shaped tool with external thread and the locking screw are screwed to the expander, it is quite easy to cause the expander to expand outward, from which unexpected expansion at patient's surgical opening might be inevitable.

(2) In order to implant the screw, position the spinal connecting rod, lock the locking screw, and remove the expander, different tools must be applied. As such, the entire surgical procedure would become extremely complicated.

(3) Since, only through operator's experience and feeling, the tightness of the locking screw by the screw driver can be understood, thus two ill situations are usually met. One is that the spinal connecting rod isn't sufficiently locked due to insufficient tightness at the locking screw, and another is that the locking screw or fixing seat shall be replaced due to excessive tightening or screw slips at the locking screw.

Accordingly, how to develop a "bone screw kit" that is simple in structure, easy to operate, and can properly tighten the locking screw to the spinal connecting rod without causing damage to patient's surgical opening is an urgent problem for those in the relevant technical field.

SUMMARY

In one embodiment of this disclosure, a bone screw kit includes:

a support member, including a bottom portion and two wings, the bottom portion having a hole, the two wings being oppositely disposed and parallel to each other and extending in a first direction to protrude over a top surface of the bottom portion, each of the two wings having an internal wall furnished with a first internal thread, a concave portion being formed between the bottom portion and the two wings;

a screw, having a thread portion, pivotally disposed at the bottom portion, the thread portion penetrating through the hole of the bottom portion to swing out of the bottom portion;

an extension sleeve, including a connecting piece and two extension wings, the two extension wings being oppositely disposed at the connecting piece and parallel to each other and extending in the first direction, each of the two extension wings having an external wall furnished with a first external thread, engagement structures being furnished between the internal wall of each of the two extension wings and the corresponding external wall of each of the two wings, the extension sleeve sleeving the two wings of the support member in the first direction, the internal wall of each of the two extension wings being engaged with the corresponding external wall of each of the two wings via the engagement structures;

a connecting rod, disposed between the two wings and axially perpendicular to the first direction;

a screw driver, having axially and oppositely a first axial end and a second axial end, an external wall of the first axial end of the screw driver being furnished with a plurality of ribs, each of the plurality of ribs having a longitudinal direction parallel to the first direction, the first axial end of the screw driver being furnished with a first snap protruding out of the plurality of ribs in the first direction, the first snap having an end with a first outer diameter close to the plurality of ribs and another end with a second outer diameter away from the plurality of ribs, the second outer diameter being less than the first outer diameter;

a locking screw, shaped as a ring, having oppositely a third axial end and a fourth axial end, having a through hole extending in the first direction, an internal wall of the locking screw being furnished with a plurality of grooves parallel to each other and extending in the first direction, an external wall of the locking screw being furnished with a second external thread, a second snap being provided to the third axial end of the through hole close to the locking screw, the second snap having a first inner diameter less than the first outer diameter but larger than the second outer diameter; wherein the first axial end of the screw driver is inserted into the through hole of the locking screw in the first direction, the plurality of ribs are correspondingly engaged with the plurality of grooves, the first snap are engaged with the second snap with a length of the first snap being protruded out of the third axial end, and thus the screw driver is engaged with the locking screw; wherein the screw driver rotates the locking screw to engage the second external thread and the first internal thread so as to clip the connecting rod between the locking screw and the bottom portion; and an extension sleeve remover, including a socket having two opposite axial ends having an opening and an innermost cavity, respectively, an internal wall of the socket being furnished with a second internal thread, the socket being to sleeve the extension sleeve via the second internal thread engaging the first external thread; wherein the socket is rotated to have the second axial end of the screw driver to contact against the innermost cavity so as to separate the extension sleeve from the support member.

Further scope of applicability of the present application will become more apparent from the detailed description given hereinafter. However, it should be understood that the detailed description and specific examples, while indicating exemplary embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The present disclosure will become more fully understood from the detailed description given herein below and the accompanying drawings which are given by way of illustration only, and thus are not limitative of the present disclosure and wherein.

DETAILED DESCRIPTION

Figure 1:
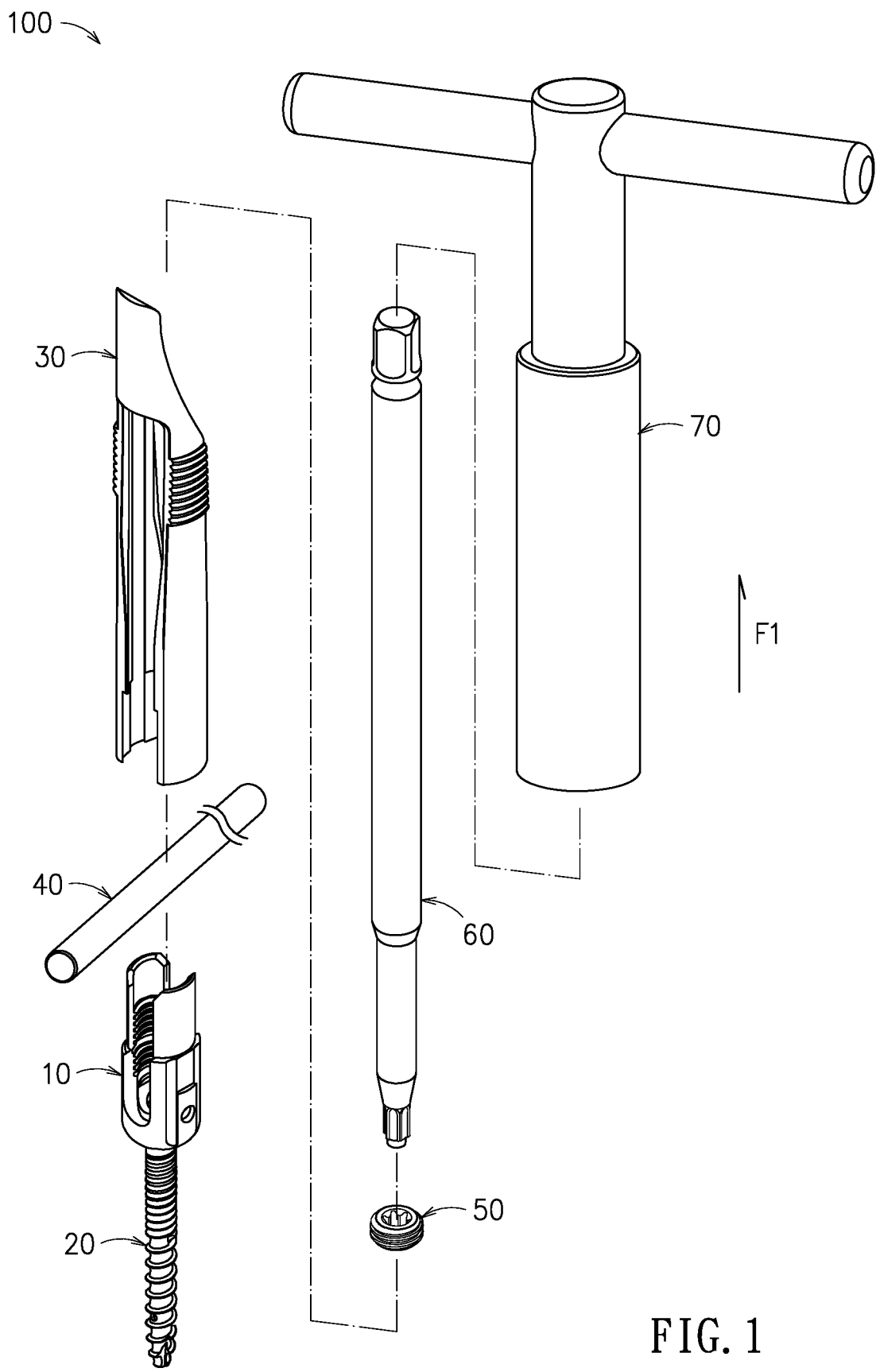
FIG. 1 is a schematic exploded view of an embodiment of the screw kit in accordance with this disclosure.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

Referring to FIG. 1, a bone screw kit 100 of this embodiment includes a support member 10, a screw 20, an extension sleeve 30, a connecting rod 40, a locking screw 50, a screw driver 60 and an extension sleeve remover 70.

It shall be explained that a length of the connecting rod 40 is determined per practical requirements. In FIG. 1, only part of the connecting rod 40 is shown, and generally the length of the connecting rod 40 shall meet the requirement to connect two said neighboring bone screw kits 100.

Referring to FIG. 1 through FIG. 5, the support member 10 includes a bottom portion 11 and two wings 12. The bottom portion 11 has a hole 13. The wings 12 are individually parallel to the first direction F1, and each of the wings 12 has a fixation portion 121 and a breakable piece 122, in which the fixation portion 121 is connected with the bottom portion 11. A junction of the breakable piece 122 and the fixation portion 121 is furnished with a groove 123. The two parallel wings 12 are extended in the first direction F1 over a top surface of the bottom portion 11, and stand oppositely.

Each of the wings 12 has an internal wall furnished with a first internal thread 14. Preferably, the first internal thread 14 is extended to cover internal walls of the fixation portion 121 and the breakable piece 122.

An external wall of the fixation portion 121 in each of the wings 12 is furnished with a dovetail rack 15. A longitudinal direction of the dovetail rack 15 is parallel to the first direction F1. As such, a concave portion 16 can be formed between the bottom portion 11 and the two wings 12.

The screw 20, having a thread portion 21, is pivotally disposed at the bottom portion 11 by having the thread portion 21 to extend under a bottom surface of the bottom portion 11 via a hole 13 thereof, such that the thread portion 21 can swing with respect to the bottom portion 11 of the support member 10.

Generally, the screw 20 has an outer diameter larger than a ball head of the thread portion 21 does. The hole 13 provides an upper concavity. After the screw 20 is placed to the concave portion 16 by having the thread portion 21 to penetrate through the hole 13, the ball head of the thread portion 21 would be held by the concavity of the hole 13 so as to allow the penetrating thread portion 21 to swing beneath the bottom portion 11 of the support member 10. However, the structuring related to the aforesaid swing design is well known to a person skilled in the art, and thus details thereabout would be omitted herein.

The extension sleeve 30 is mainly consisted of a connecting piece 31 and two extension wings 32. The two extension wings 32, parallel individually to the first direction F1, are disposed to opposite sides of the connecting piece 31. Each of the extension wings 32 has an internal wall furnished with a dovetail groove 33 extending in the first direction F1. In addition, each of the extension wings 32 has an external wall furnished with a first external thread 34.

The connecting piece 31 and the two extension wings 32 of the extension sleeve are structured to have the same radian, such that the extension sleeve 30 can be formed as a cylindrical structure.

The first external thread 34 at the external wall of the extension wing 32 is disposed at one end of the extension wing 32 close to the connecting piece 31.

By sleeving the extension sleeve 30 to the two wings 12 of the support member in the first direction F1, each of the dovetail grooves 33 would engage the corresponding dovetail rack 15.

Figure 2:
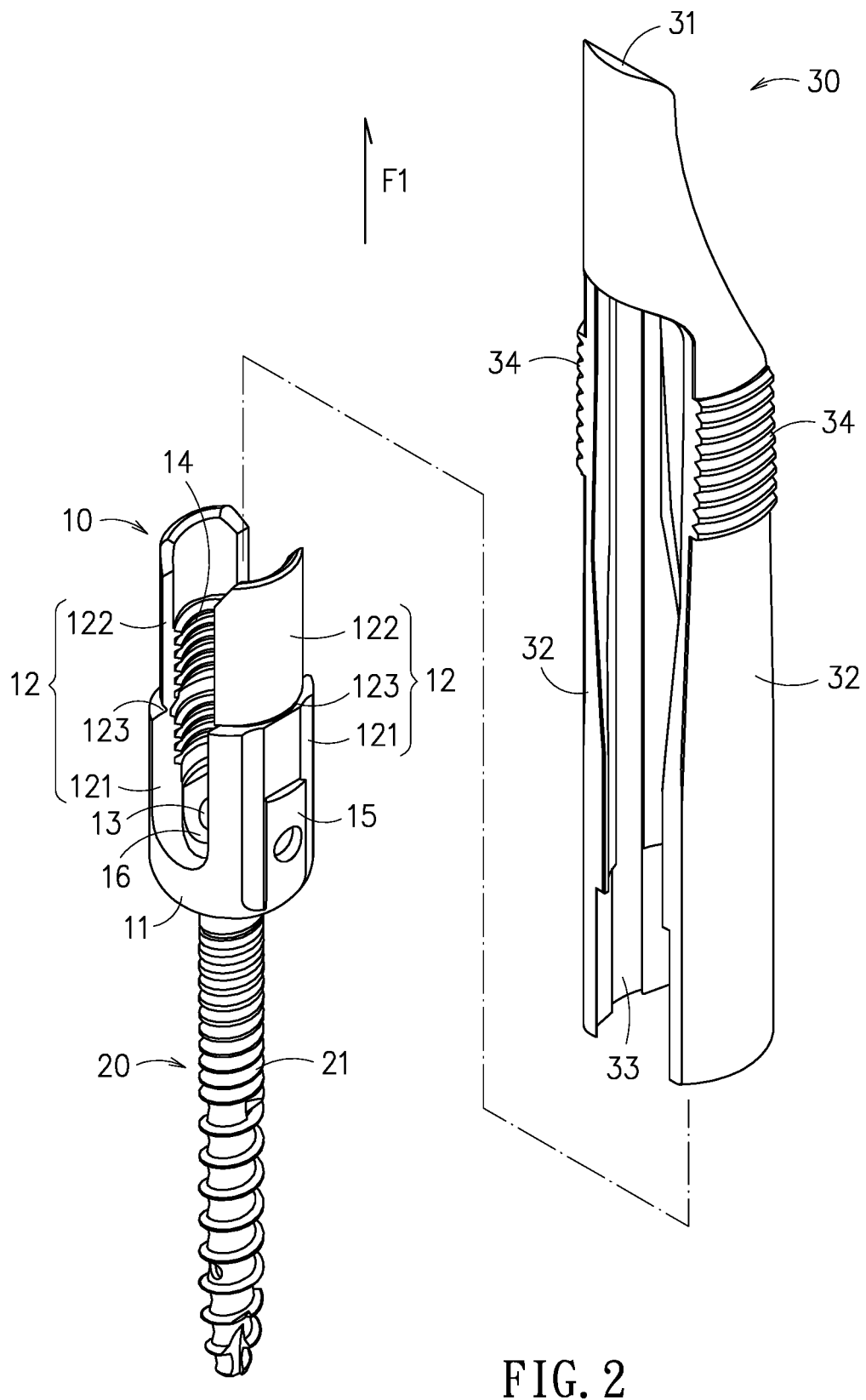
FIG. 2 and FIG. 3 demonstrate schematically connections of the support member, the screw and the extension sleeve in respective exploded views in accordance with this disclosure.
Figure 3:
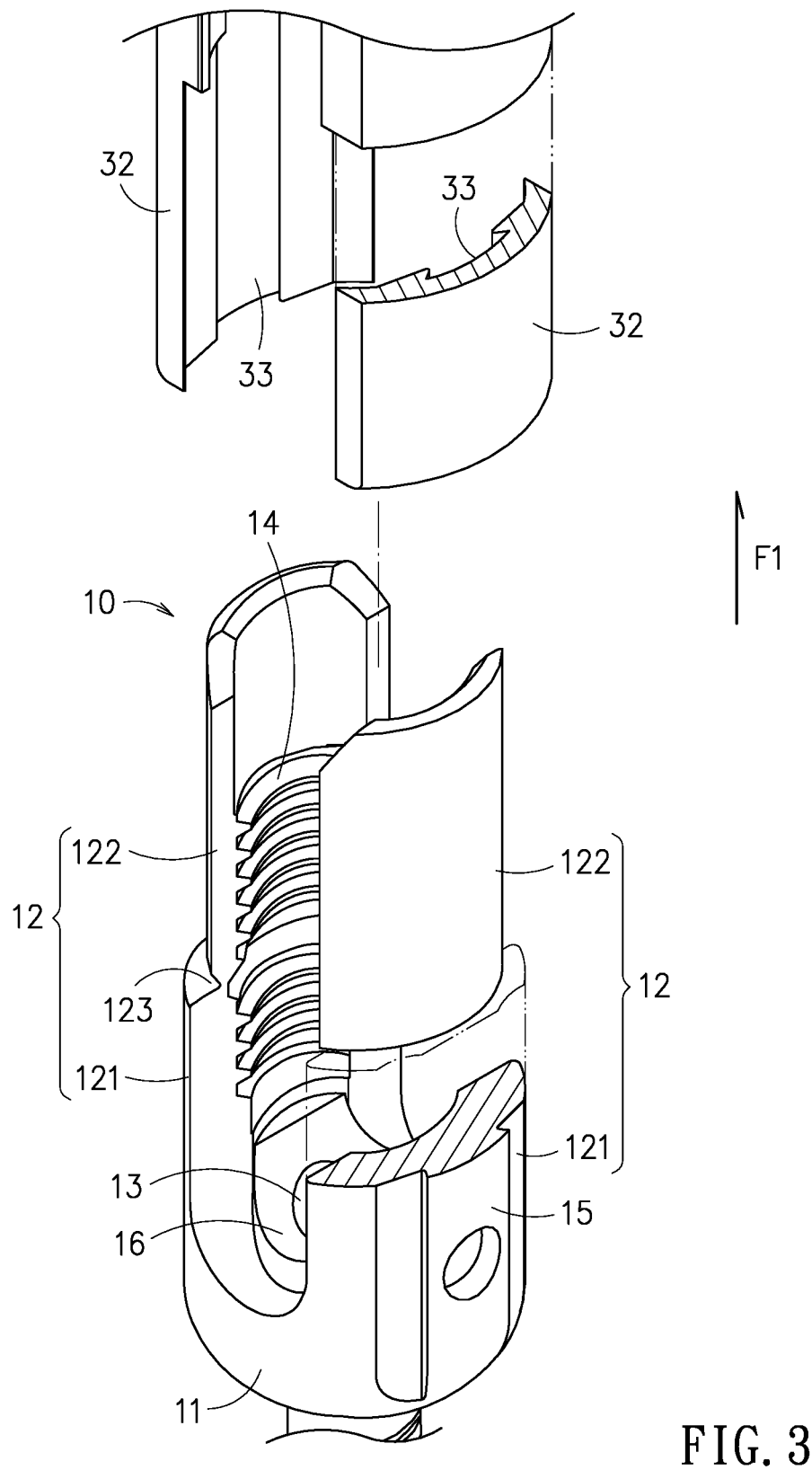

It shall be explained that, in this embodiment, the pairing of the dovetail rack 15 and the dovetail groove 33 is simply one of various examples for engaging the internal wall of the extension wing 32 and the external wall of the wing 12 in accordance with this embodiment. In FIG. 2, the dovetail racks 15 are provided individually to the corresponding external walls of the respective wings 12, and the corresponding dovetail grooves 33 are provided to the internal walls of the respective extension wings 32. In addition, the aforesaid arrangement of the dovetail grooves 33 and the dovetail racks 15 can be switched off to another arrangement of the dovetail racks 15 and the dovetail grooves 33. Namely, in another embodiment, the dovetail groove 33 can be provided to the external wall of the wing 12, while the corresponding dovetail rack 15 is provided to the internal wall of the extension wing 32. Further, in some other embodiments, the internal wall of the extension wing 32 and the corresponding external wall of the respective wing 12 can be furnished with some other engagement structures in the art, such as groove-and-rack pairs and hole-and-node pairs. In particular, the number and types of the engagement structures are not limited thereto.

Before the extension sleeve 30 is sleeved onto the support member 10, the connecting rod 40 can be placed between the two wings 12 in a direction perpendicular to the first direction F1, by having the support member 10 to support the connecting rod 40.

Figure 4:
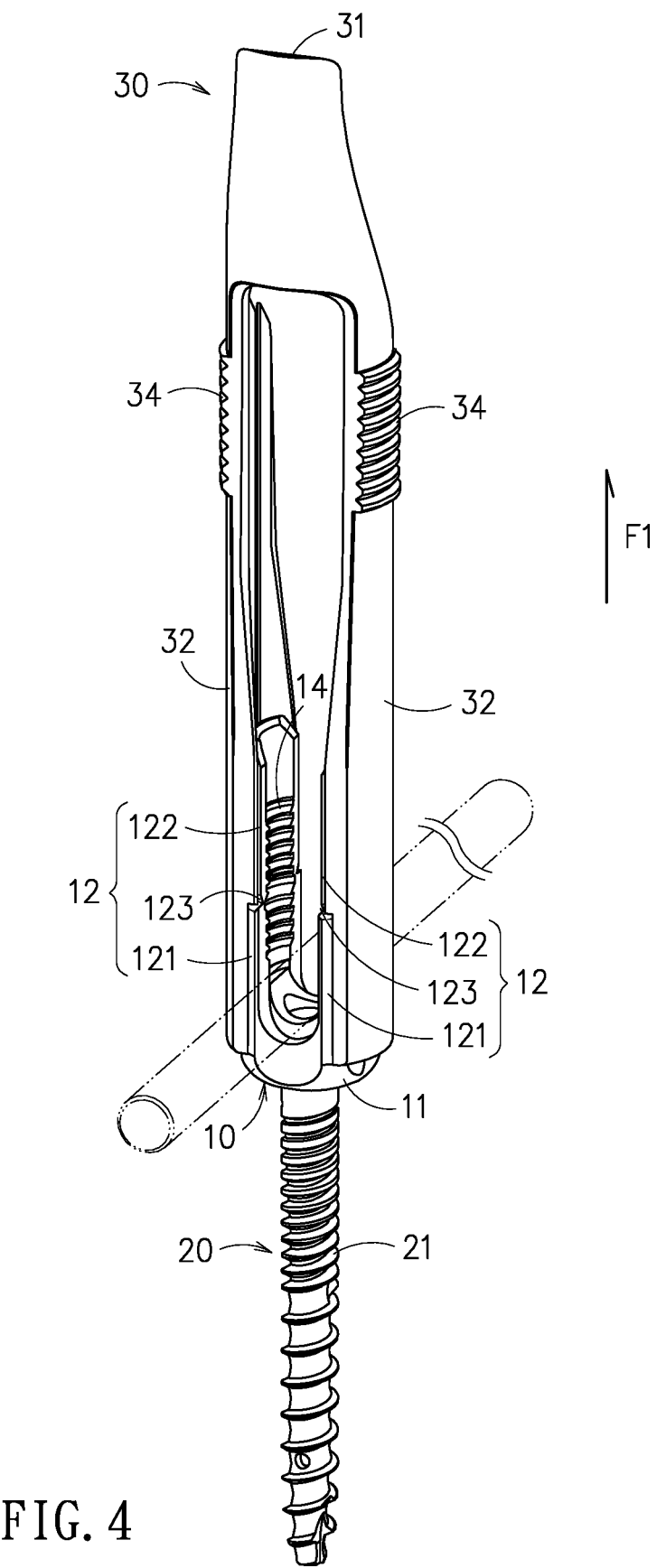
FIG. 4 and FIG. 5 demonstrate schematically connections of the support member, the screw and the extension sleeve in respective assembled views in accordance with this disclosure.
Figure 5:
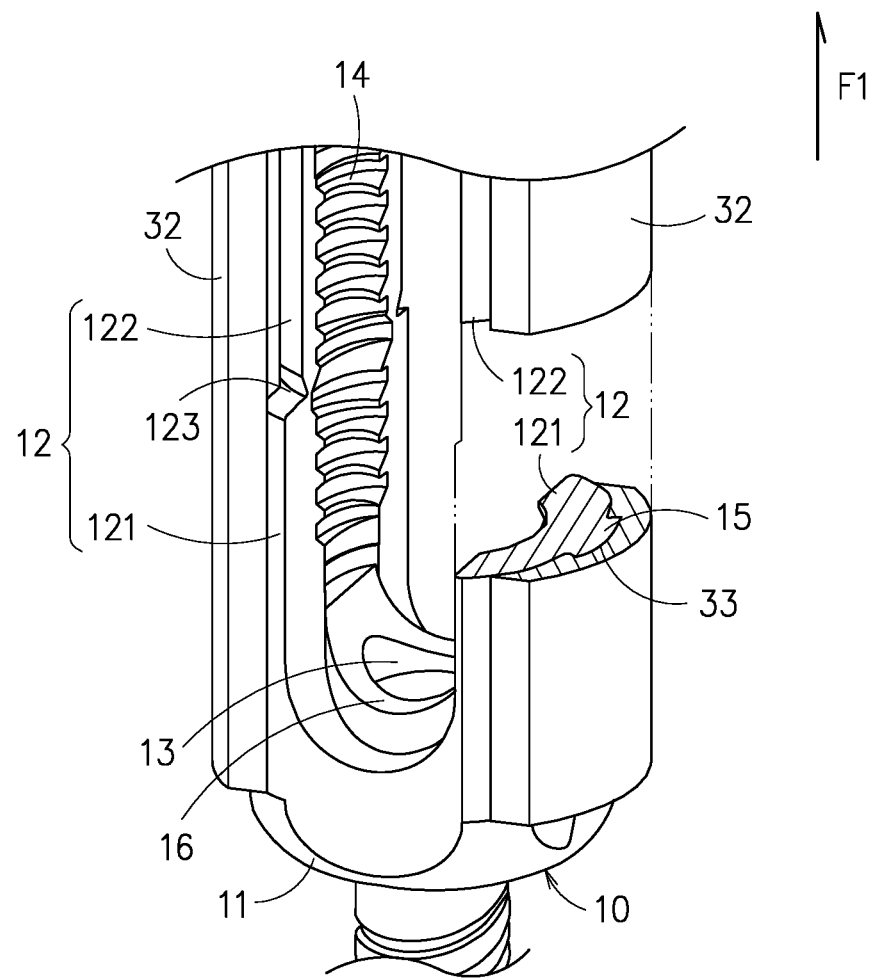
Figure 6:
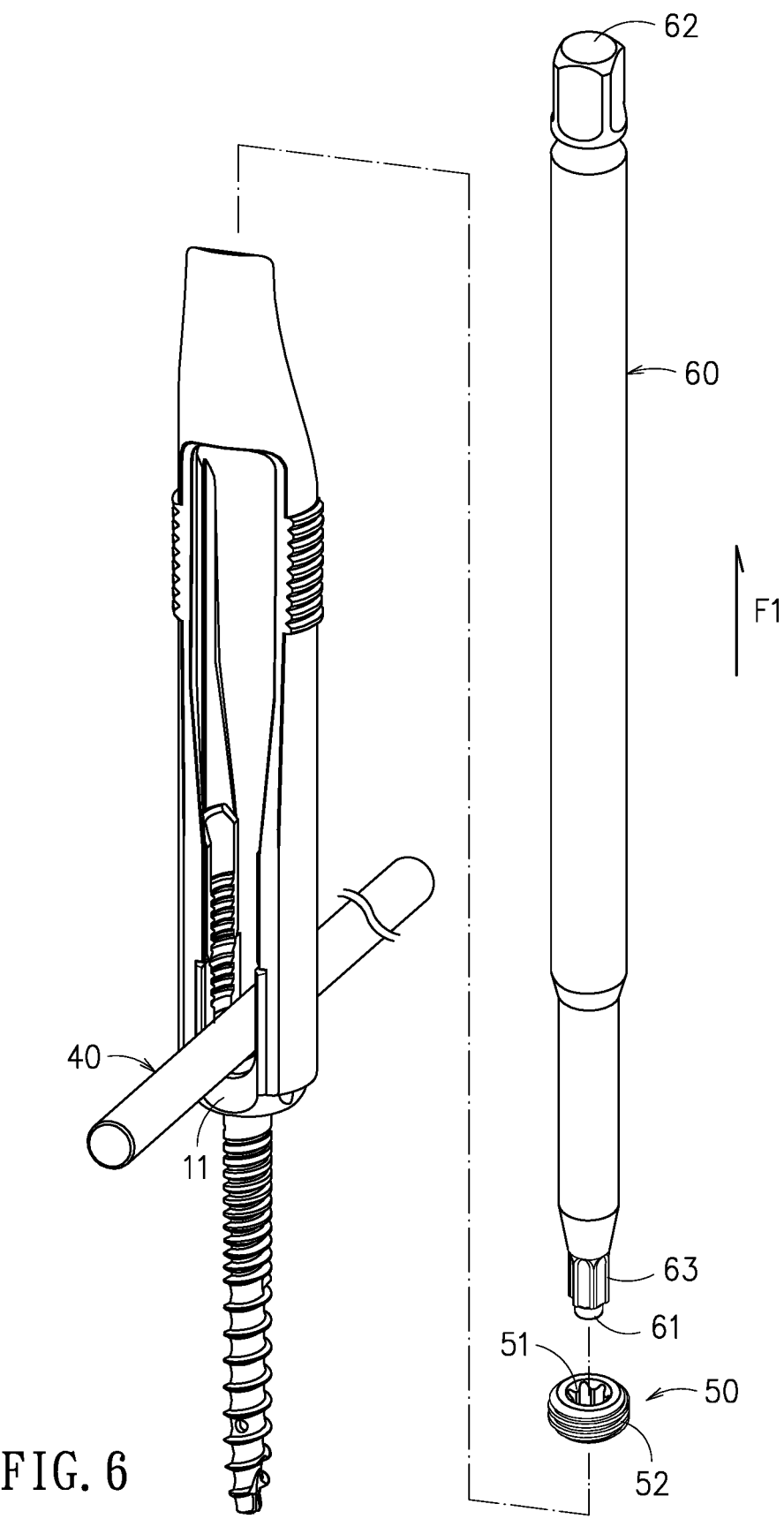
FIG. 6 is a schematic exploded view of the locking screw and screw driver in accordance with this disclosure.
Figure 7:
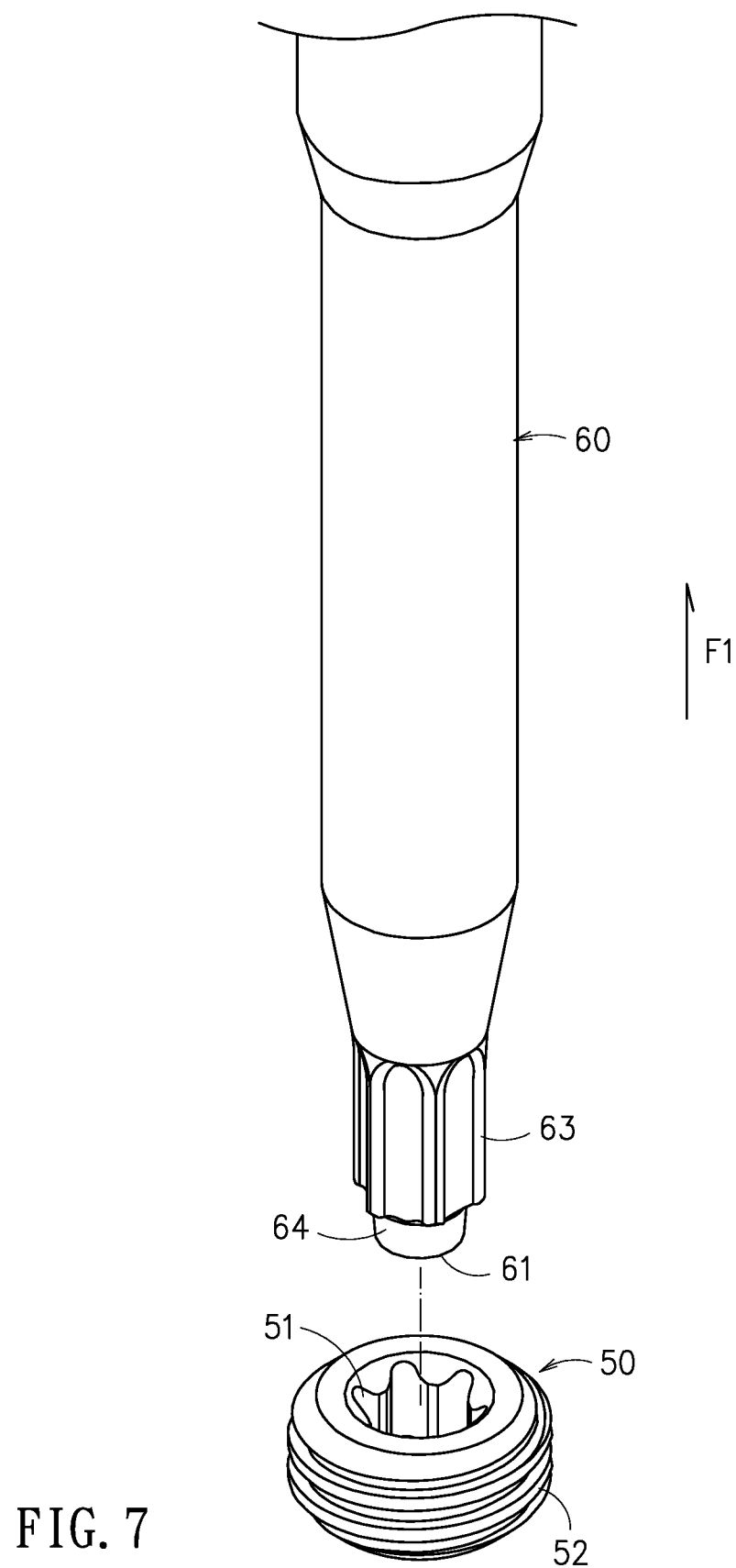
FIG. 7 is a schematic enlarged exploded view showing the locking screw and part of the screw driver prior to engagement.
Figure 8:
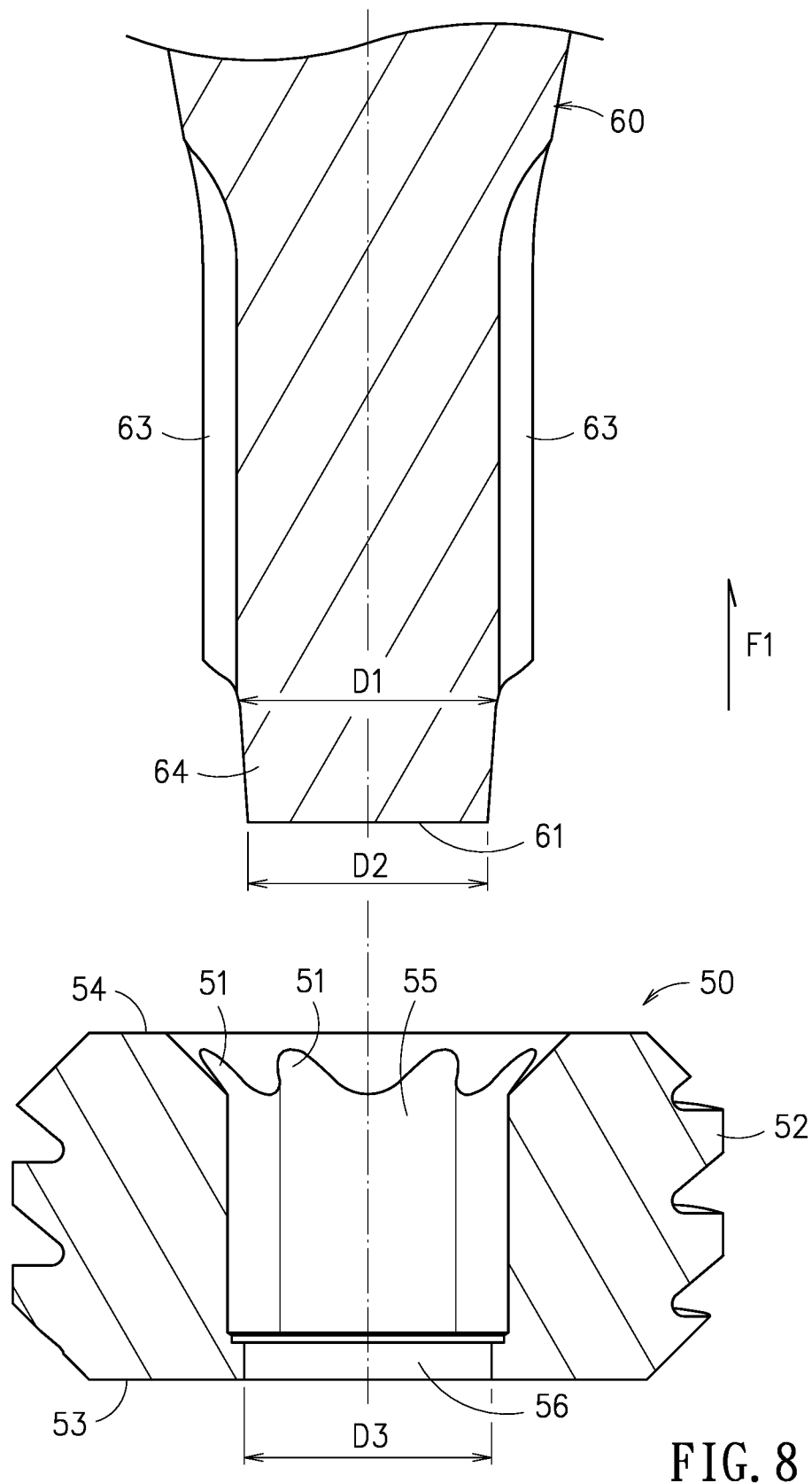
FIG. 8 is a schematic axial cross-sectional view of FIG. 7.
Figure 9:
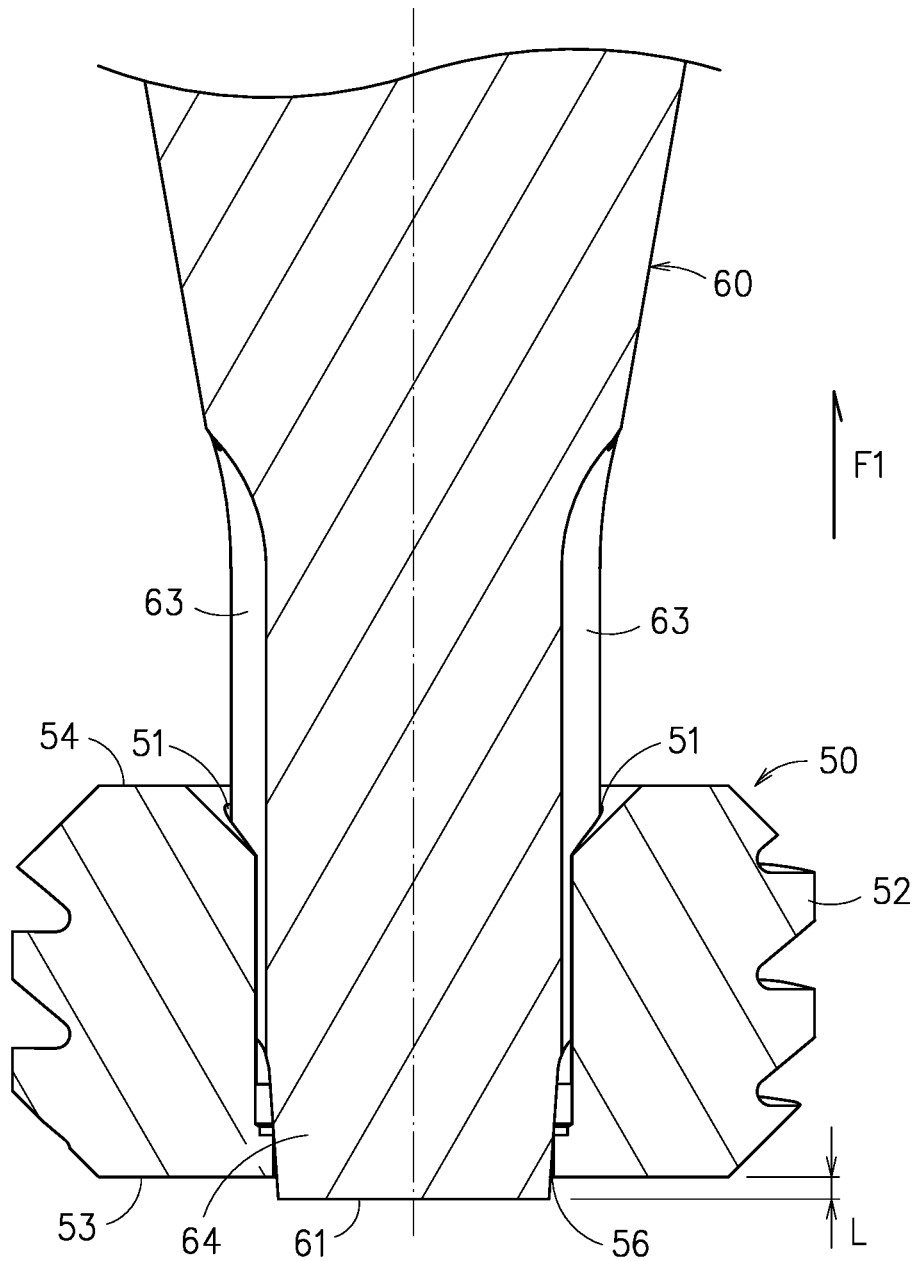
FIG. 9 is a schematic assembled view of FIG. 8.

Referring to FIG. 6, after the assembling of FIG. 4 is finished, then the locking screw 50 and the screw driver 60 can be engaged.

Refer now to FIG. 6 through FIG. 9. The screw driver 60 has oppositely a first axial end 61 and a second axial end 62 axially. The external wall of the first axial end 61 of the screw driver 60 is furnished with a plurality of ribs 63. Each of the ribs 63 is extended longitudinally in parallel to the first direction F1.

The first axial end 61 of the screw driver 60 has a first snap 64 shaped as a free round end. The first snap 64, protruded out of the plurality of ribs 63, is symmetrically structured with respect to a central line parallel to the first direction F1. The first snap 64 has a first outer diameter D1 at the end thereof close to the plurality of ribs 63, while another end thereof away from the plurality of ribs 63 has a second outer diameter D2. In particular, the second outer diameter D2 is less than the first outer diameter D1.

The locking screw 50, shaped as a ring, has oppositely a third axial end 53 and a fourth axial end 54. The locking screw 50 has a central through hole 55 extended in the first direction F1.

The internal wall of the locking screw 50 is furnished with a plurality of parallel grooves 51, and each of the grooves 51 is extended in a direction parallel to the first direction F1. On the other hand, the external wall of the locking screw 50 is furnished with a second external thread 52.

The third axial end 53 of the through hole 55 of the locking screw 50 has a second snap 56 shaped to be a round hole. The second snap 56 has a first inner diameter D3, less than the first outer diameter D1 but larger than the second outer diameter D2.

While the screw driver 60 is plugged into the through hole 55 of the locking screw 50 in a direction parallel to the first direction F1, the first axial end 61 is extended over the third axial end 53, with each of the ribs 63 to be fitted between the neighboring grooves 51. Since the first inner diameter D3 is less than the first outer diameter D1 but larger than the second outer diameter D2, thus the first snap 64 can pass the through hole 55 to engage the second snap 56, with a length L of the first snap 64 protruded out of the third axial end 53, such that the screw driver 60 and the locking screw 50 can achieve a connection state. Preferably, the length L is ranged within 0.2-0.5 mm.

In this disclosure, the screw driver 60 can be applied to screw the locking screw 50. Since the screw driver 60 and the locking screw 50 are provided individually with the first snap 64 and the second snap 56, respectively, thus the screw driver 60 can be applied to "grasp" the locking screw 50. After the screw driver 60 is inserted into the through hole 55 of the locking screw 50 in a direction parallel to the first direction F1, the locking screw 50 can be arbitrarily moved by the screw driver 60. Namely, no additional tool is needed to grasp the locking screw 50.

Figure 10:
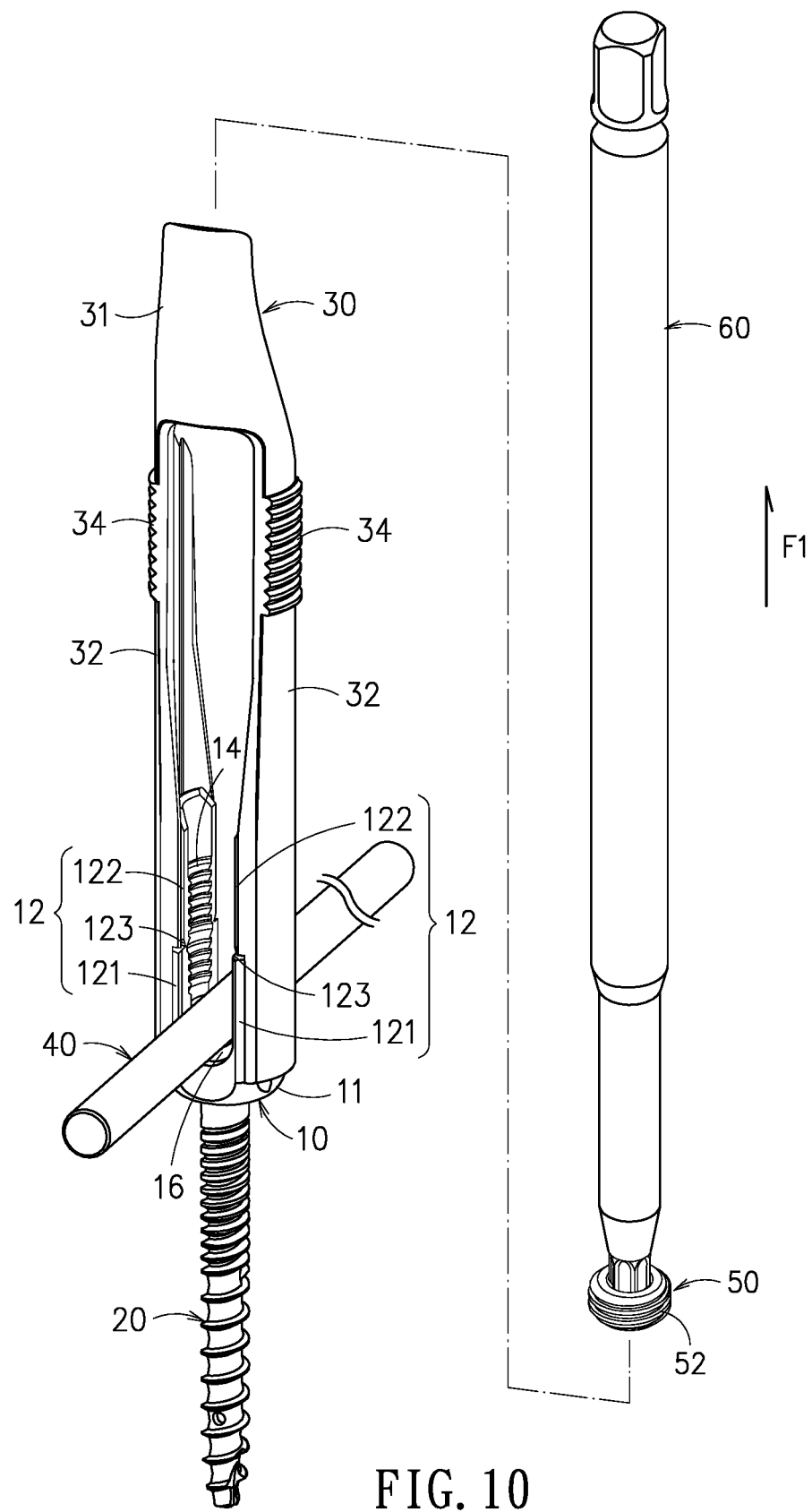
FIG. 10 shows schematically another state of FIG. 6 with the locking screw engaged to the screw driver.
Figure 11:
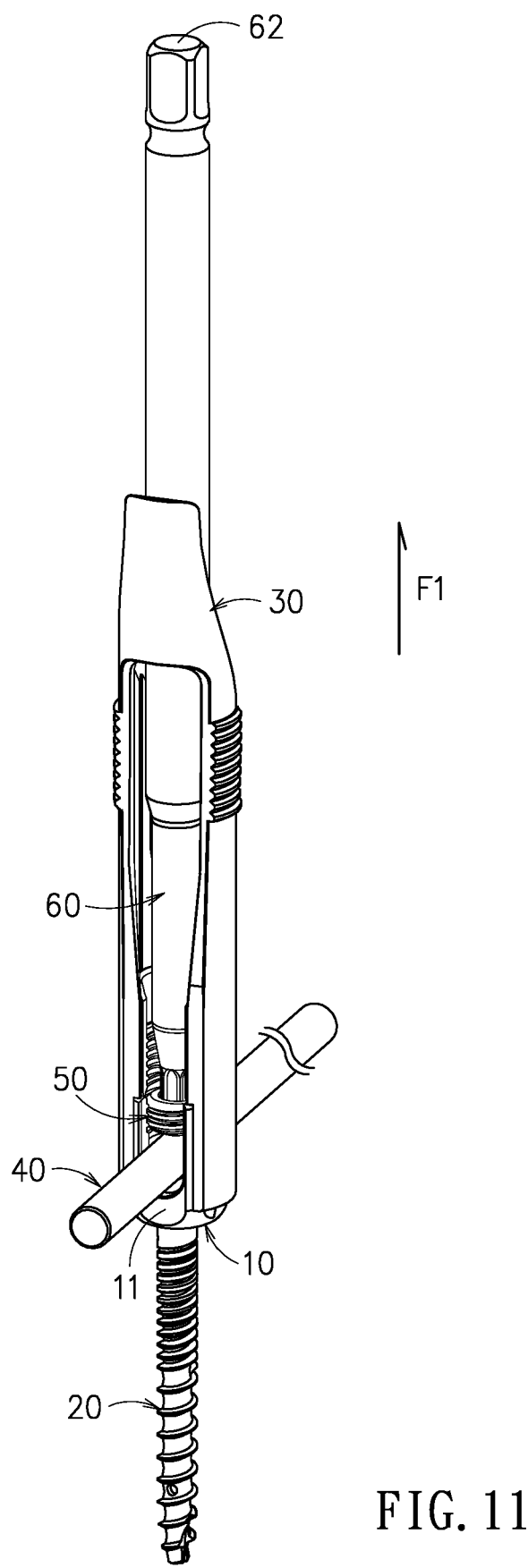
FIG. 11 shows schematically a further state of FIG. 6 with the locking screw, the screw driver, the extension sleeve and the support member engaged together.

Refer to FIG. 10 and FIG. 11. The assembly of the screw driver 60 and the locking screw 50 is placed into the extension sleeve 30. As described above, the screw driver 60 of this disclosure, used to screw the locking screw 50, can grasp the locking screw to arbitrarily move, without any other tool.

Then, the screw driver 60 is applied to screw the locking screw 50 for engaging the second external thread 52 and the first internal thread 14, such that the connecting rod can be clipped between the locking screw 50 and the bottom portion 11.

Figure 12:
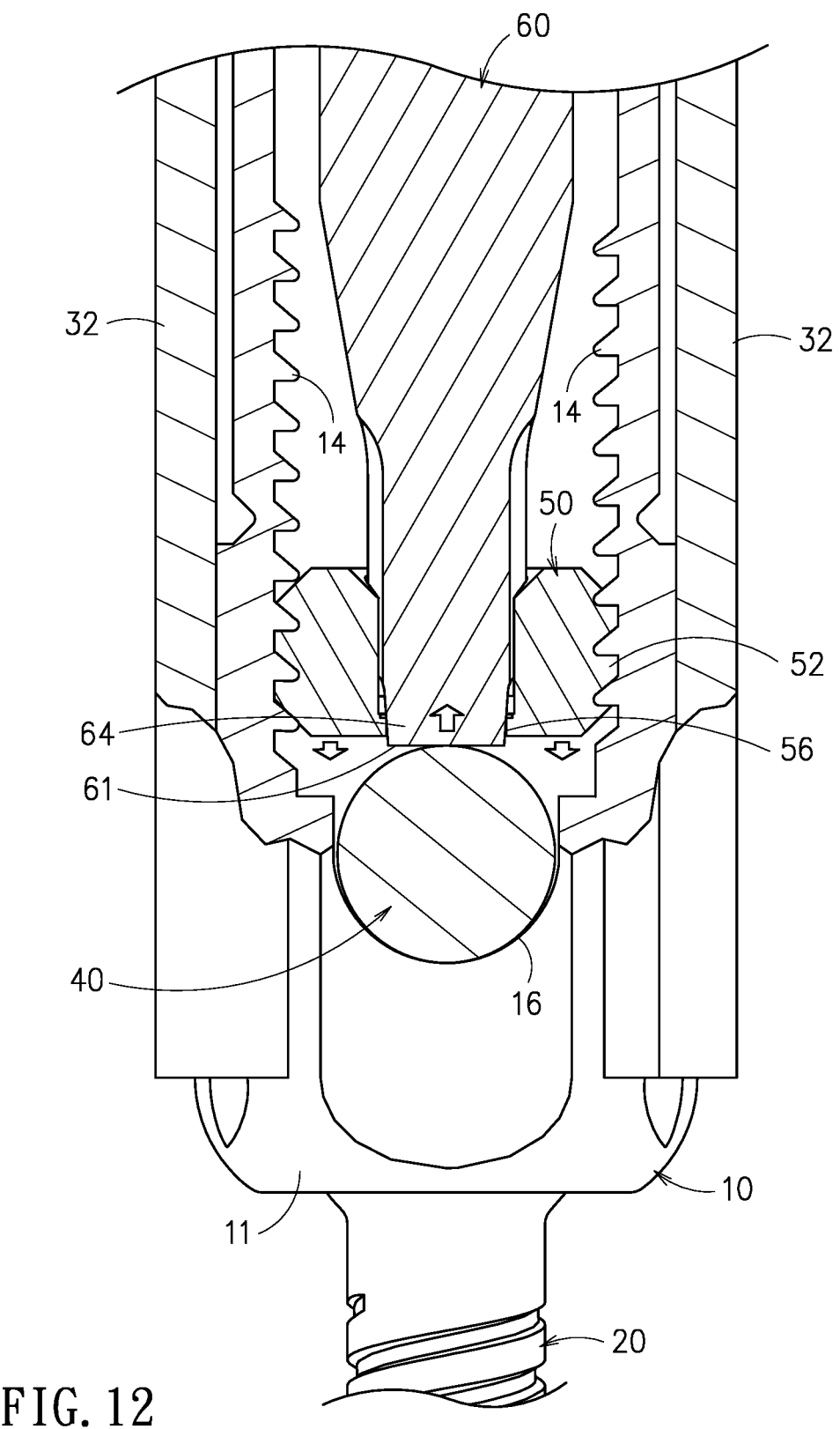
FIG. 12 is a schematic axial cross-sectional view showing the engagement of the locking screw, the screw driver, the extension sleeve and the support member engaged together, with the first axial end contacted against the connecting rod, in accordance with this disclosure.
Figure 13:
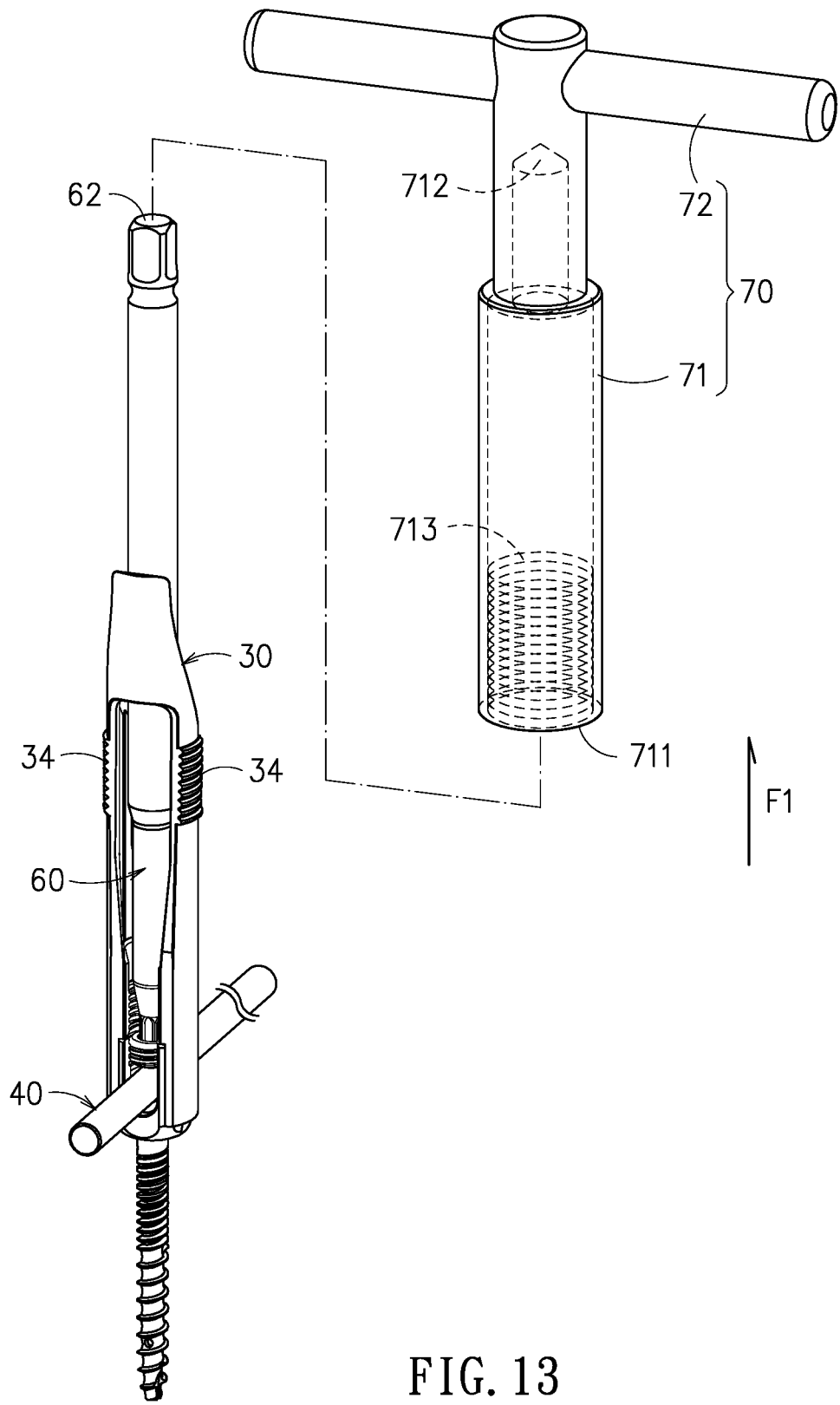
FIG. 13 demonstrates schematically the extension sleeve remover and the extension sleeve, prior to engagement, in accordance with this disclosure.
Figure 14:
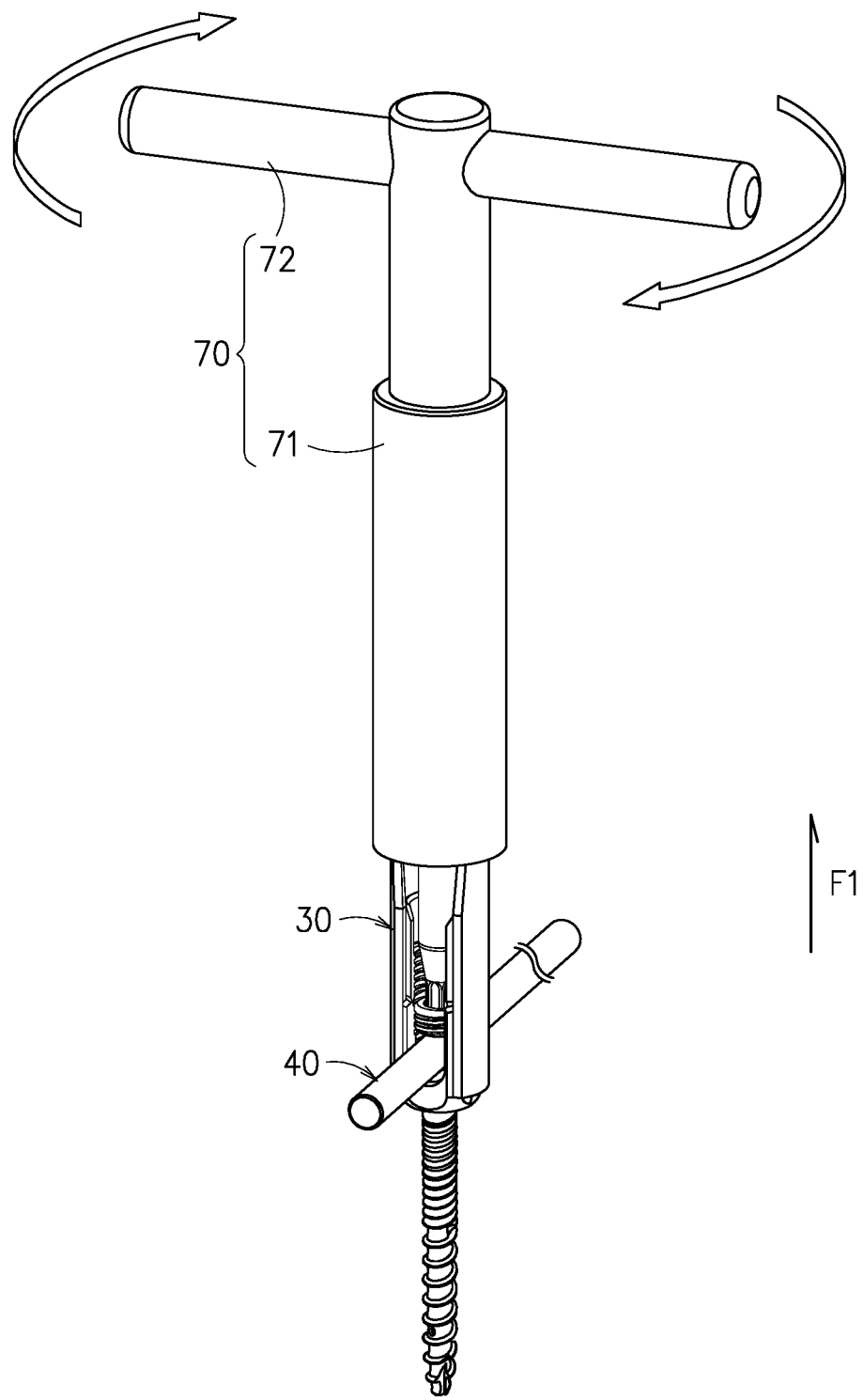
FIG. 14 demonstrates schematically rotation of the extension sleeve remover in accordance with this disclosure.
Figure 15:
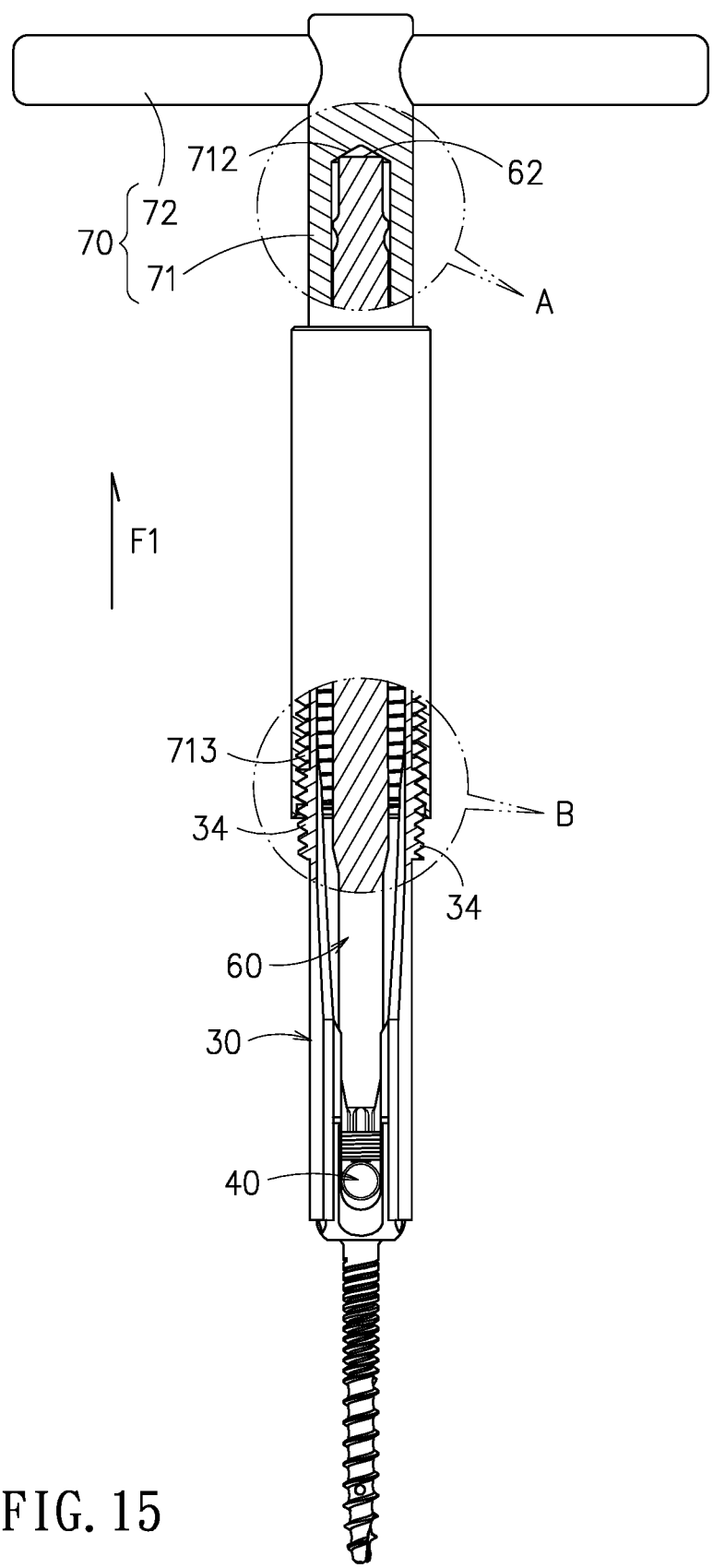
FIG. 15 is another view of FIG. 14 showing schematically parts thereof in axial cross-sectional views.

Refer now to FIG. 12, by which the operation between the screw driver and the locking screw would be elucidated. While in applying the screw driver 60 to engage the second external thread 52 and the first internal thread 14, the locking screw 50 can be screwed downward in the first direction F1. When the locking screw 50 is continuously screwed downward to make the first axial end 61 contact the connecting rod 40. With the connecting rod 40 being tightly clipped between the first axial end 61 and the concave portion 16, if the screw driver 60 is continuously rotated to screw down the locking screw then, since the connecting rod 40 is there to stop the downward movement of the first axial end 61, the first axial end 61 would be reversely forced to separate the first snap 64 from the second snap 56.

In addition, after the locking screw 50 is driven by the screw driver 60 to depress upon the connecting rod 40, since this time the screw driver 60 would be pushed back by the connecting rod 40, thus the locking screw 50 can be sure to tightly contact against the connecting rod 40. Thereupon, the following two situations won't occur. One situation is that the locking screw 50 is less tightened to depress the connecting rod 40, and another is that the screw driver 60 fastens the locking screw 50 too much to result in unexpected screw slips.

After the assembly shown in FIG. 11 is complete, it implies that the locking screw 50 is locked, and the connecting rod 40 is fixed between the support member 10 and the locking screw 50. Then, referring to FIG. 1, and FIG. 13 through FIG. 15, the extension sleeve remover 70 can be applied to remove the extension sleeve 30.

Referring also to FIG. 1, and FIG. 13 through FIG. 15, the extension sleeve remover 70 is consisted of a socket 71 and a handle 72. The handle 72, configured as a round rod, has a longitudinal axis perpendicular to an extension axis of the socket 71.

Two opposite axial ends of the socket 71 are furnished with an opening 711 and an innermost cavity 712, respectively. The handle 72 is disposed at the axial end of the socket 71 having the innermost cavity 712. The socket 71 has an internal wall furnished with a second internal thread 713. After the socket 71 sleeves the extension sleeve 30, the handle 72 (also the socket 71) can be rotated to have the second internal thread 713 to engage the first external thread 34.

Referring to FIG. 14 to FIG. 17, after the extension sleeve remover 70 sleeves the extension sleeve 30, the handle 72 as well as the socket 71 can rotate the second internal thread 713 to engage the first external thread 34. By having the extension sleeve remover to move downward in the first direction F1, the second axial end 62 of the screw driver can contact against the innermost cavity 712.

Figure 16A:
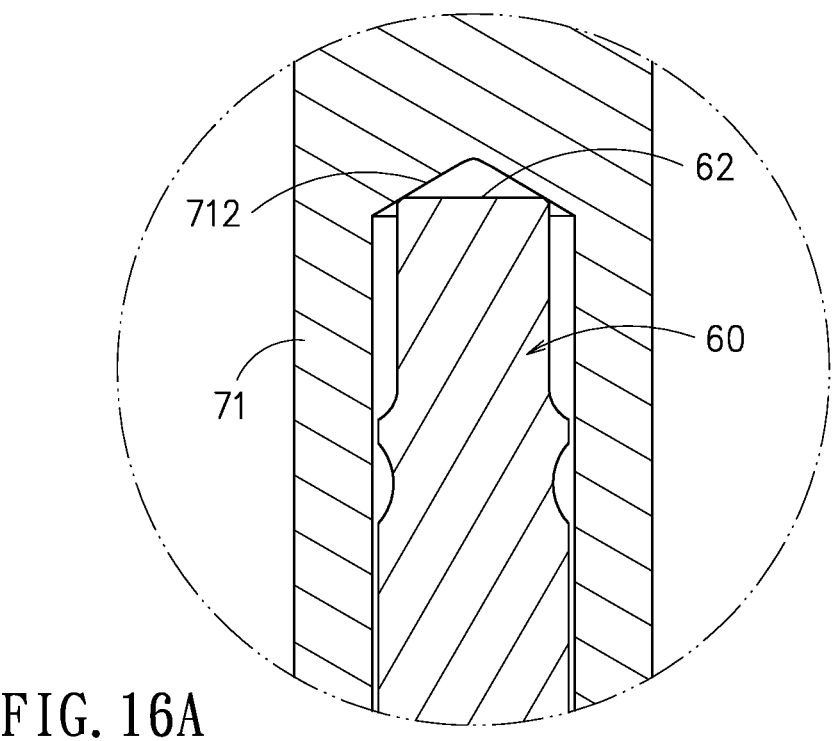
FIG. 16A is a schematic enlarged view of circle A of FIG. 15.

As shown in FIG. 16A, the innermost cavity 712 is shown to have a conic end, and the second axial end 62 has its external sidewall to contact against the innermost cavity 712. In this disclosure, the second axial end 62 can be arbitrarily configured, but meeting a requirement that the second axial end 62 shall contact against the innermost cavity 712 fully or partially, at one or multiple points, or by one or multiple sides. Whatever the contact style is, it is not limited to the illustrated form as shown in the listed embodiments herein.

Figure 16B:
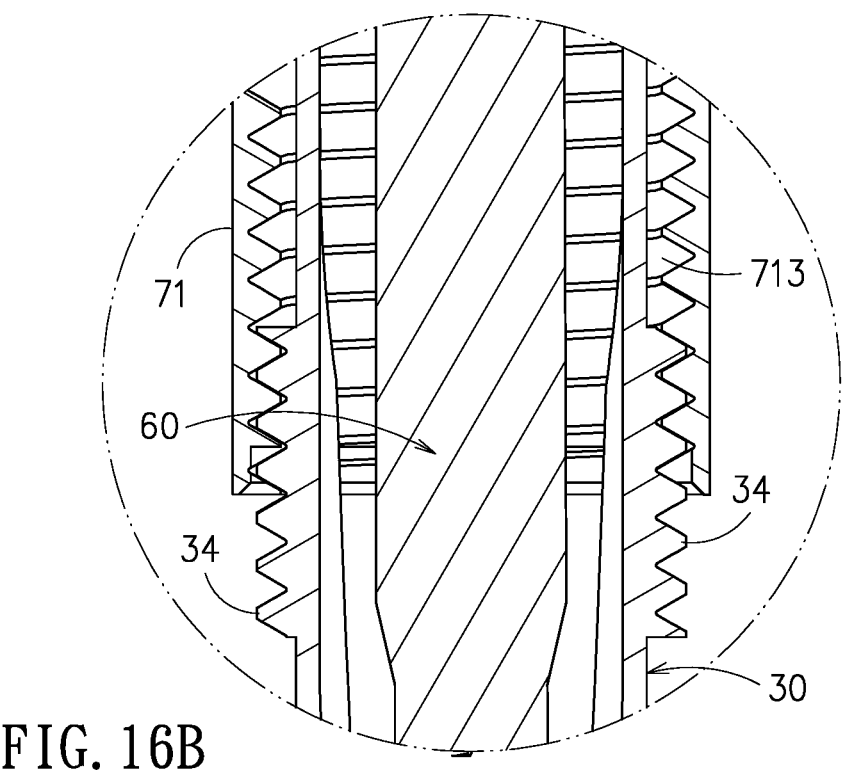
FIG. 16B is a schematic enlarged view of circle B of FIG. 15.
Figure 17:
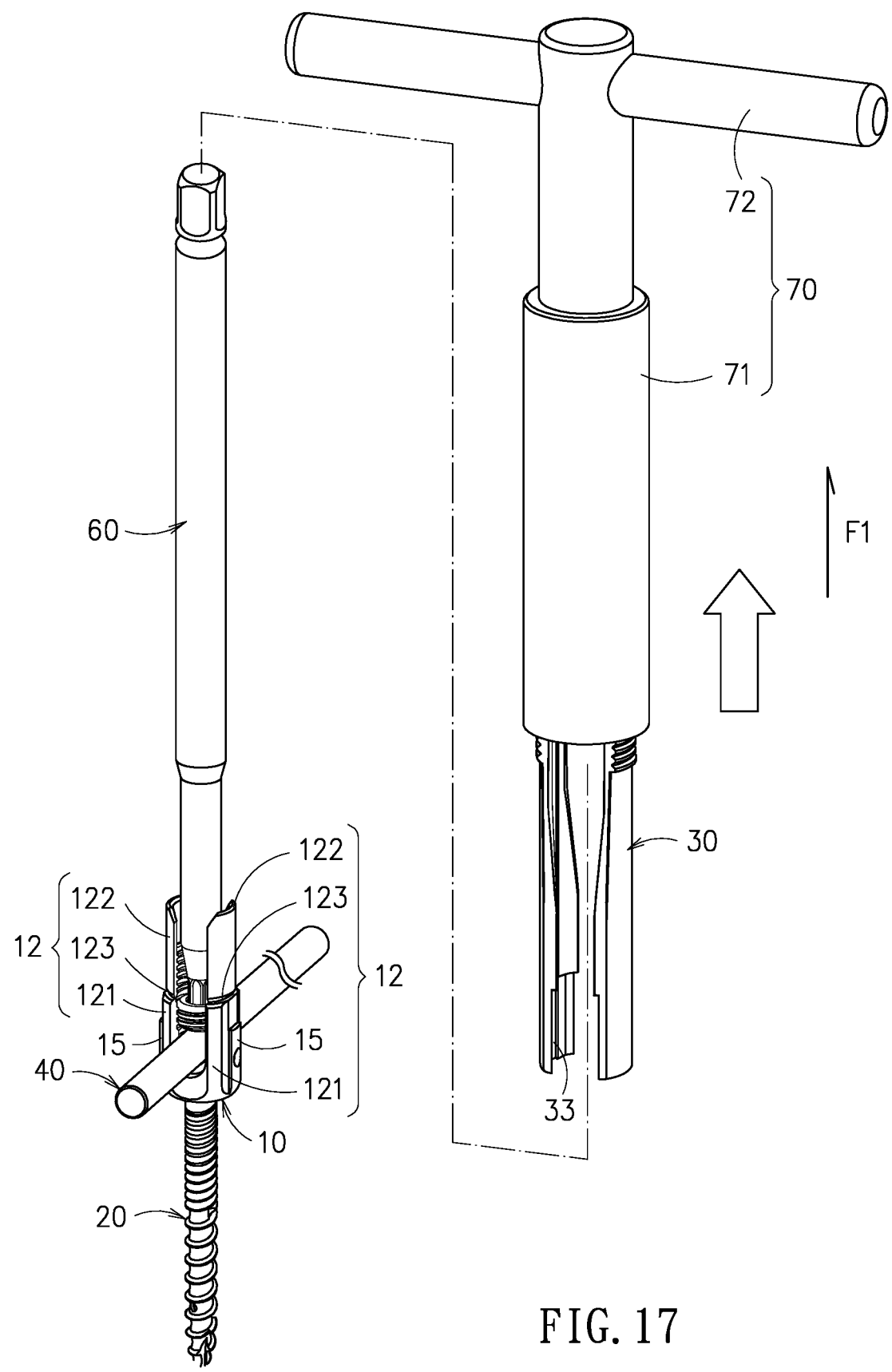
FIG. 17 shows schematically disengagement of the extension sleeve and the support member by the extension sleeve remover in accordance with this disclosure.

Then, the handle 72 as well as the socket 71 can be rotated further. Since the downward movement of the extension sleeve remover 70 would be stopped by the screw driver 60, and the extension sleeve 30 and the support member 10 are detachably engaged via the pairing of the dovetail groove 33 and the dovetail rack 15, thus, with the second internal thread 713 to keep engaging the first external thread 34 as shown in FIG. 16B, the extension sleeve remover 70 can vertically retrieve the extension sleeve 30 in the first direction F1. Finally, the extension sleeve 30 can be moved away from the two wings 12 of the support member 10, as shown in FIG. 17.

After completing all the foregoing operations, the following steps can be performed, such as removing of the screw driver 60, and breaking of the breakable pieces 122 of the wings 12 at the corresponding grooves 123.

In summary, in the bone screw kit provided by this disclosure, the extension sleeve 30 is detachably engaged with the support member 10 through the dovetail groove 33 and the dovetail rack 15, and specific movable relationships among the extension sleeve remover 70, the extension sleeve 30 and the screw driver 60 are also provided. In addition, a special engagement design is to the screw driver and the locking screw so as to surely depress the locking screw upon the spinal connecting rod, without causing damages to patient's surgical openings. Thus, advantages in simple structuring, convenient operations and no damage to human can be obtained.

With respect to the above description then, it is to be realized that the optimum dimensional relationships for the parts of the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present disclosure.

What is claimed is:

1. A bone screw kit, comprising:
   a support member, including a bottom portion and two wings, the bottom portion having a hole, the two wings being oppositely disposed and parallel to each other and extending in a first direction to protrude over a top surface of the bottom portion, each of the two wings having an internal wall furnished with a first internal thread, a concave portion being formed between the bottom portion and the two wings;
   a screw, having a thread portion, pivotally disposed at the bottom portion, the thread portion penetrating through the hole of the bottom portion to swing out of the bottom portion;
   an extension sleeve, including a connecting piece and two extension wings, the two extension wings being oppositely disposed at the connecting piece and parallel to each other and extending in the first direction, each of the two extension wings having an external wall furnished with a first external thread, engagement structures being furnished between the internal wall of each of the two extension wings and the corresponding external wall of each of the two wings, the extension sleeve sleeving the two wings of the support member in the first direction, the internal wall of each of the two extension wings being engaged with the corresponding external wall of each of the two wings via the engagement structures;

a connecting rod, disposed between the two wings and axially perpendicular to the first direction;

a screw driver, having axially and oppositely a first axial end and a second axial end, an external wall of the first axial end of the screw driver being furnished with a plurality of ribs, each of the plurality of ribs having a longitudinal direction parallel to the first direction, the first axial end of the screw driver being furnished with a first snap protruding out of the plurality of ribs in the first direction, the first snap having an end with a first outer diameter close to the plurality of ribs and another end with a second outer diameter away from the plurality of ribs, the second outer diameter being less than the first outer diameter;

a locking screw, shaped as a ring, having oppositely a third axial end and a fourth axial end, having a through hole extending in the first direction, an internal wall of the locking screw being furnished with a plurality of grooves parallel to each other and extending in the first direction, an external wall of the locking screw being furnished with a second external thread, a second snap being provided to the third axial end of the through hole close to the locking screw, the second snap having a first inner diameter less than the first outer diameter but larger than the second outer diameter; wherein the first axial end of the screw driver is inserted into the through hole of the locking screw in the first direction, the plurality of ribs are correspondingly engaged with the plurality of grooves, the first snap are engaged with the second snap with a length of the first snap being protruded out of the third axial end, and thus the screw driver is engaged with the locking screw; wherein the screw driver rotates the locking screw to engage the second external thread and the first internal thread so as to clip the connecting rod between the locking screw and the bottom portion; and an extension sleeve remover, including a socket having two opposite axial ends having an opening and an innermost cavity, respectively, an internal wall of the socket being furnished with a second internal thread, the socket being to sleeve the extension sleeve via the second internal thread engaging the first external thread; wherein the socket is rotated to have the second axial end of the screw driver to contact against the innermost cavity so as to separate the extension sleeve from the support member.

2. The bone screw kit of claim 1, wherein the length of the first snap out of the third axial end is ranged between 0.2-0.5 mm.

3. The bone screw kit of claim 1, wherein the engagement structures include:
    a dovetail rack, provided to an external wall of each of the wings, having a longitudinal direction parallel to the first direction; and
    a dovetail groove, provided to an internal wall of each of the extension wings, having a longitudinal direction parallel to the first direction; wherein the extension sleeve sleeves the two wings of the support member in the first direction, and each of the dovetail grooves is engaged with one said dovetail rack.

4. The bone screw kit of claim 3, wherein each of the wings parallel to the first direction has a fixation portion and a breakable piece, the fixation portion is connected with the bottom portion, and a junction between the breakable piece and the fixation portion is formed as a groove.

5. The bone screw kit of claim 4, wherein the dovetail rack of the external wall of each of the wings is disposed at the fixation portion.

6. The bone screw kit of claim 4, wherein the first internal thread is extended to cover an internal wall of the fixation portion and another internal wall of the breakable piece.

7. The bone screw kit of claim 1, wherein the connecting piece and the two extension wings of the extension sleeve have the same radian, and the extension sleeve is formed as a cylindrical structure.

8. The bone screw kit of claim 1, wherein the first external thread of the external wall of each of the extension wings is disposed at one end of each of the extension wings close to the connecting piece.

9. The bone screw kit of claim 1, wherein an external wall of the first axial end of the screw driver is furnished with a plurality of ribs individually extending in the first direction, the locking screw is shaped as a ring, and an internal wall of the locking screw is furnished with a plurality of grooves individually extending in the first direction; wherein, when the first axial end of the screw driver is inserted into the locking screw, the plurality of ribs are engaged correspondingly with the plurality of grooves so as to have the first axial end to connect the locking screw.

10. The bone screw kit of claim 1, wherein the extension sleeve remover includes a handle disposed at the axial end of the socket having the innermost cavity; wherein, by continuously rotating the handle, the second axial end of the screw driver would contact against the innermost cavity so as to have the extension sleeve to separate from the two wings of the support member.

* * * * *